United States Patent [19]
Kristinsson

[11] Patent Number: 5,139,525
[45] Date of Patent: Aug. 18, 1992

[54] PROSTHETIC FOOT

[76] Inventor: Össur Kristinsson, P.O. Box 5288, 125 Reykjavik, Iceland

[21] Appl. No.: 812,852

[22] Filed: Dec. 23, 1991

Related U.S. Application Data

[63] Continuation of Ser. No. 560,728, Jul. 31, 1990, abandoned.

[30] Foreign Application Priority Data

Jul. 31, 1989 [SE] Sweden ............................. 8902628

[51] Int. Cl.⁵ ............................................. A61F 2/66
[52] U.S. Cl. ........................................ 623/55; 623/50; 623/51; 623/52
[58] Field of Search ................................. 623/53–56, 623/47–52

[56] References Cited

U.S. PATENT DOCUMENTS

| | | | |
|---|---|---|---|
| 694,324 | 2/1902 | Peer | 623/53 X |
| 810,180 | 1/1906 | Wintermute | 623/55 |
| 827,720 | 8/1906 | Erwin | 623/54 X |
| 2,475,372 | 7/1949 | Catranis | 623/49 |
| 4,413,360 | 11/1983 | Lamb et al. | 623/53 X |
| 4,959,073 | 9/1990 | Merlette | 623/55 |

FOREIGN PATENT DOCUMENTS

| | | | |
|---|---|---|---|
| 363006 | of 0000 | France | 623/55 |
| 11828 | 10/1899 | Sweden | 623/55 |
| 145674 | 6/1954 | Sweden | 623/53 |
| 0778732 | 12/1980 | U.S.S.R. | 623/55 |
| 0806023 | 2/1981 | U.S.S.R. | 623/55 |
| 0135625 | 12/1919 | United Kingdom | 623/53 |
| 0795732 | 5/1958 | United Kingdom | 623/53 |
| 2216423 | 10/1989 | United Kingdom | 623/53 |

Primary Examiner—Randall L. Green
Assistant Examiner—D. Willse
Attorney, Agent, or Firm—Bacon & Thomas

[57] ABSTRACT

The invention relates to a prosthetic foot, including a hollow cosmesis (7) with a spring (1) fixed therein, and extending in the longitudinal direction of the foot for operative connection to an adapter (4) for connection to a leg prosthesis (5). The spring (1) is adapted to absorb energy on heel strike and to release this energy on toe-off. In accordance with the invention the spring (1) includes at least one spring element (8) which in the rear portion of the foot has a curved portion in a vertical direction, and a snubbing element in association with the curved spring portion or portions (15). The snubbing element (11) has at least one convex curved surface portion with a smaller curvature than the opposing inside of the curved spring portion (15), and is arranged such that when spring element (8) is deflected on loading the prosthetic foot, an increasing part thereof comes into engagement against surface portions of the snubbing element (11) with corresponding foreshortening of the free springing portion or portions of the spring element (8), to produce increased spring resistance to increased load on the foot.

10 Claims, 6 Drawing Sheets

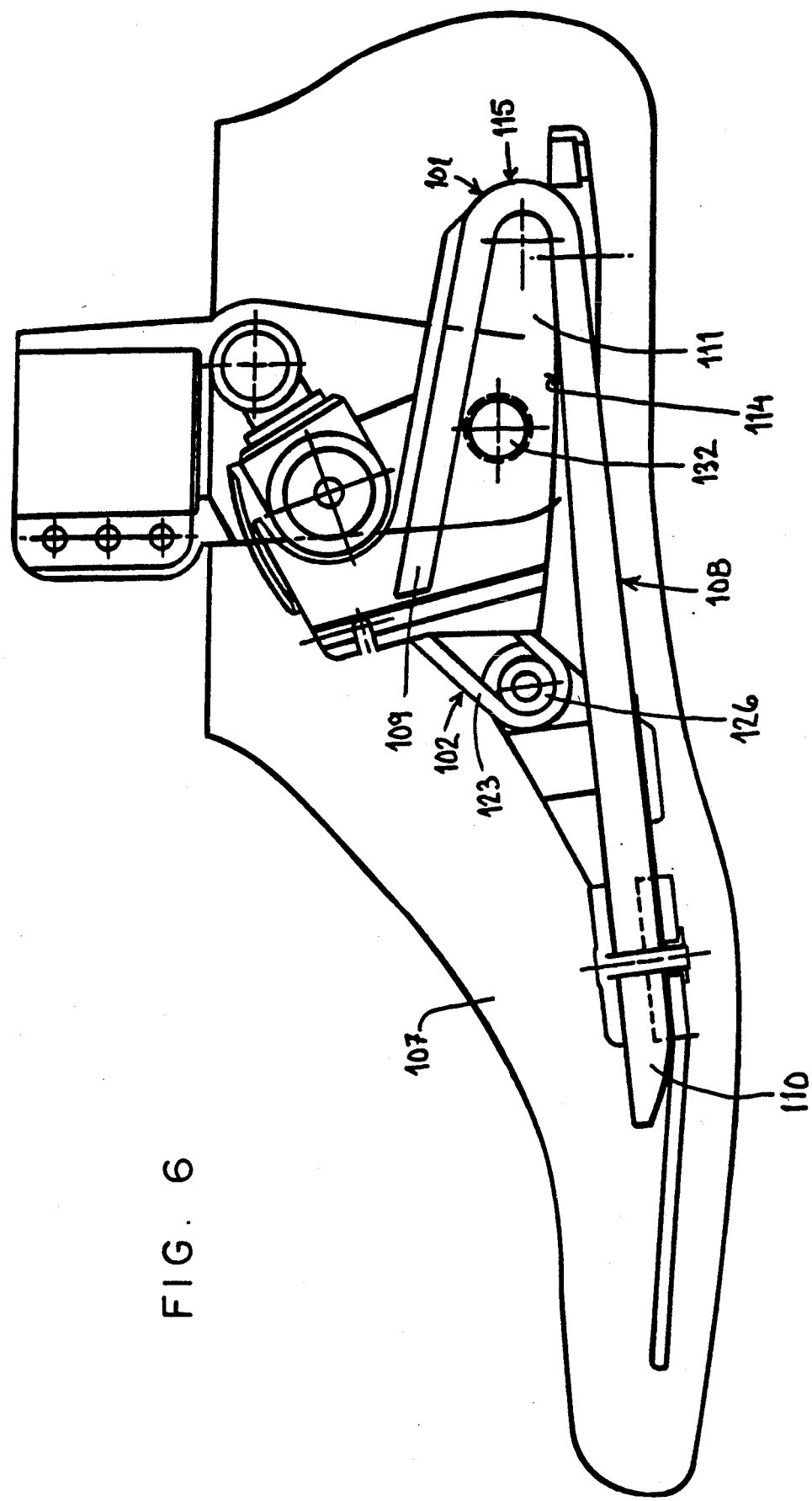

PROSTHETIC FOOT

This application is a continuation of application Ser. No. 560,728, filed Jul. 31, 1990, now abandoned.

The present invention relates to the prosthetic field, and more specifically to an improved prosthetic foot.

BACKGROUND ART

The development of new light materials with high mechanical performance has made it possible to produce prosthetic feet, which to a considerably greater extent than previously; liken the natural foot with regard to movement pattern while at the same time enabling the operative force to be stored and regained with decreased loss of energy.

While earlier prosthetic feet were either relatively stiff or were flexible to absorb energy, they limited the user to relatively slow and less strenuous activities, such as walking etc. Prosthetic feet have more recently been produced having an elastic core which stores energy when the foot is put on a substructure (heel strike), and gives up this energy as the foot is thrust away from the substructure (toe-off), thus simulating the active plantar flexion of the natural foot. This enables more demanding activities such as tennis, running etc.

An example of this kind of foot is described in the U.S. Pat. No. 4,547,913 and is sold under the trade name Flex-Foot by Flex-Foot Inc., Irvine, Calif. USA; This foot is made from carbon fibre composite material including a leg portion, a foot portion and a heel portion, all of which are stiffly connected to each other, and all three being spring elements with considerable elastic flexibility which enables the release of absorbed energy and permits the amputee to participate in sports activities, e.g. running or tennis. In a commercial embodiment, the foot portion is integrated with the leg portion and extends downwards and forwards from the ankle region, while the heel portion is a member attached to the lower part of the leg portion such as to extend downwards-backwards from the ankle region. In another commercial variant, the heel portion is substantially flat and extends backwards from approximately the middle part of the foot portion to which it is attached.

A prosthetic foot which is based on similar principles is the so-called SEATTLE foot (U.S. Pat. No. 4,645,509) where the lower leg part is fastened to an energy storing spring member with the shape of approximately a U placed horizontally with the opening forwards. Here lower leg part is fastened to the upper somewhat shorter leg of the U with the lower leg of the U fixed in the foot cosmesis.

A somewhat different type of prosthesis with an energy storing core is described in British Patent No. 2 187 102. The prosthetic foot described here has a first spring member extending from the heel to the forward part of the foot, and which is intended to store and release energy on being loaded by normal body movements. For taking up larger loads, there is arranged a second spring member above, and at some distance from the first one, so that when there is sufficient load the first member is bent into engagement against the second member, subsequent to which both spring members are deflected together.

A disadvantage with the above described energy storing and energy releasing prosthetic foot types is, inter alia, that the foot must be adjusted to the individual patient both in respect of this person's weight and the desired activity which the foot shall perform. This means that a prosthesis intended for use in relatively demanding activities, e.g. running or tennis, will not be as comfortable for normal activities such as normal ambulation, due to the required spring stiffness, and vice versa.

In addition, these known prosthetic feet do not provide any damping of the return movement of the foot, resulting in the risk of resonance phenomena. Further disadvantages include defective absorption of torsional loading, i.e. turning the foot, with subsequent risk of sliding between the prosthesis sleeve and the amputation stump; and relatively heavy deformation of the foot sole is when the foot is deflected.

OBJECT OF THE INVENTION

The present invention has the object of reducing or obviating the above mentioned and other disadvantages in known prosthetic feet.

A particular object of the invention is to provide a prosthetic foot which changes its characteristics according to the load, so that it gives maximum comfort to the user in all situations.

A further object of the invention is to provide a prosthetic foot which can be adjusted to different patients and/or different activities with the aid of a simple adjustment procedure.

A still further object of the invention is to provide a prosthetic foot where the heel height (the foot attitude in relation to the lower leg when at rest) can be adjusted by the user.

These and other objects of the invention will be apparent from the following description.

SUMMARY OF THE INVENTION

In accordance with the invention, a prosthetic foot is provided which includes a hollow cosmesis and a spring means fastened therein, the means extending in the longitudinal direction of the foot and operatively connected to a leg adapter for connecting to a prosthetic leg member, the spring means being adapted such as to absorb energy on heel strike and to give up this energy on toe-off. In accordance with the invention; the spring means includes at least one spring member which includes a concave portion at the rear portion of the foot and snubbing means connected with the curved spring portion, the said snubbing means having at least one convex, curved, e.g. cylindrical, surface portion having a smaller curvature than the opposing inside of the curved spring portion. Upon flexing of the spring member or members when the prosthetic foot is loaded, an increasing part thereof comes into engagement against said curved surface portion of the snubbing means with corresponding foreshortening of the free springing portion or portions of said spring member, thereby causing stiffening of the spring member.

In accordance with one embodiment, the hook portion of the spring means has an upper forwardly extending portion arranged for coaction with an upper engagement surface of the snubbing means, and a lower portion adapted for coaction with a lower engagement surface of the snubbing means, so that for loading of the prosthetic foot the spring member portions simultaneously work against said upper and lower engagement surfaces of the snubbing means.

According to a further embodiment, the snubbing means comprises partially or wholly relatively stiff resilient material.

Due to the mentioned spring arrangement, there is not only obtained a spring which conserves the energy supplied by the heel strike and gives up this energy on toe-off, but one also which changes progressively in accordance with the load, so that the spring becomes stiffer with increased loading. Accordingly, low energy activity with low loads meet a lesser resistance than higher energy activity with high loads. A single prosthetic foot consequently will be comfortable to use for everyday ambulation and be excellently useable for different sports activities.

The spring means is preferably biased, e.g with tension straps or the like which pull the ends of the hook portion towards each other. Such biasing of the spring means eliminates risk of delamination of the spring member or members due to loading in the wrong direction, and they simultaneously provide damping of the return movement after coming down on the heel and plantar flexion. There is thus also eliminated the risk of resonance phenomena. According to a preferred embodiment of the invention the spring biasing is adjustable, so that different spring characteristics can be achieved for allowing individual adjustment of the spring characteristic to suit the individual patient.

The prosthetic foot in accordance with the invention also preferably has a defined ankle joint in the form of an ankle joint member between the leg adapter and the foot cosmesis, with which the leg adapter is associated or integrated and which is pivotably arranged about a horizontal cross axis (flexion axis) at the rear portion of the prosthetic foot. The ankle joint member has its forward swing (dorsal flexion) counteracted by stop means on the spring means, while means are also arranged for elastic restriction of backward swing of the ankle joint member (plantar flexion).

In accordance with a preferred embodiment of the prosthetic foot, its heel height, i.e. its attitude in relation to the leg prosthesis at rest, is easily adjustable, partly for compensating changed biasing of the spring means according to the above, but also to enable adjustment by the user himself for adapting the foot to different situations, e.g. barefoot ambulation or different footwear.

The above mentioned elastic means for resisting to plantar flexion can comprise the spring means itself, which can then be arranged for actuation by the ankle joint member via a linkage system or the like. Adjusting the heel height takes place by adjusting a longitudinal adjustable means, e.g. a turnbuckle included in the linkage system.

The prosthetic foot structure in accordance with the invention also permits absorption of torsional loads (lateral loads) which otherwise would be taken up by the leg sleeve and stump, with possible sliding between these two.

These and other preferred embodiments of the invention are described in more detail below.

BRIEF DESCRIPTION OF DRAWINGS

FIG. 6 is a view corresponding to the one in FIG. 2 and illustrates an alternative embodiment, corresponding parts being given the same reference numerals as in FIG. 2 with the addition of 100.

DETAILED DESCRIPTION OF PREFERRED EMBODIMENTS

Figure 1:
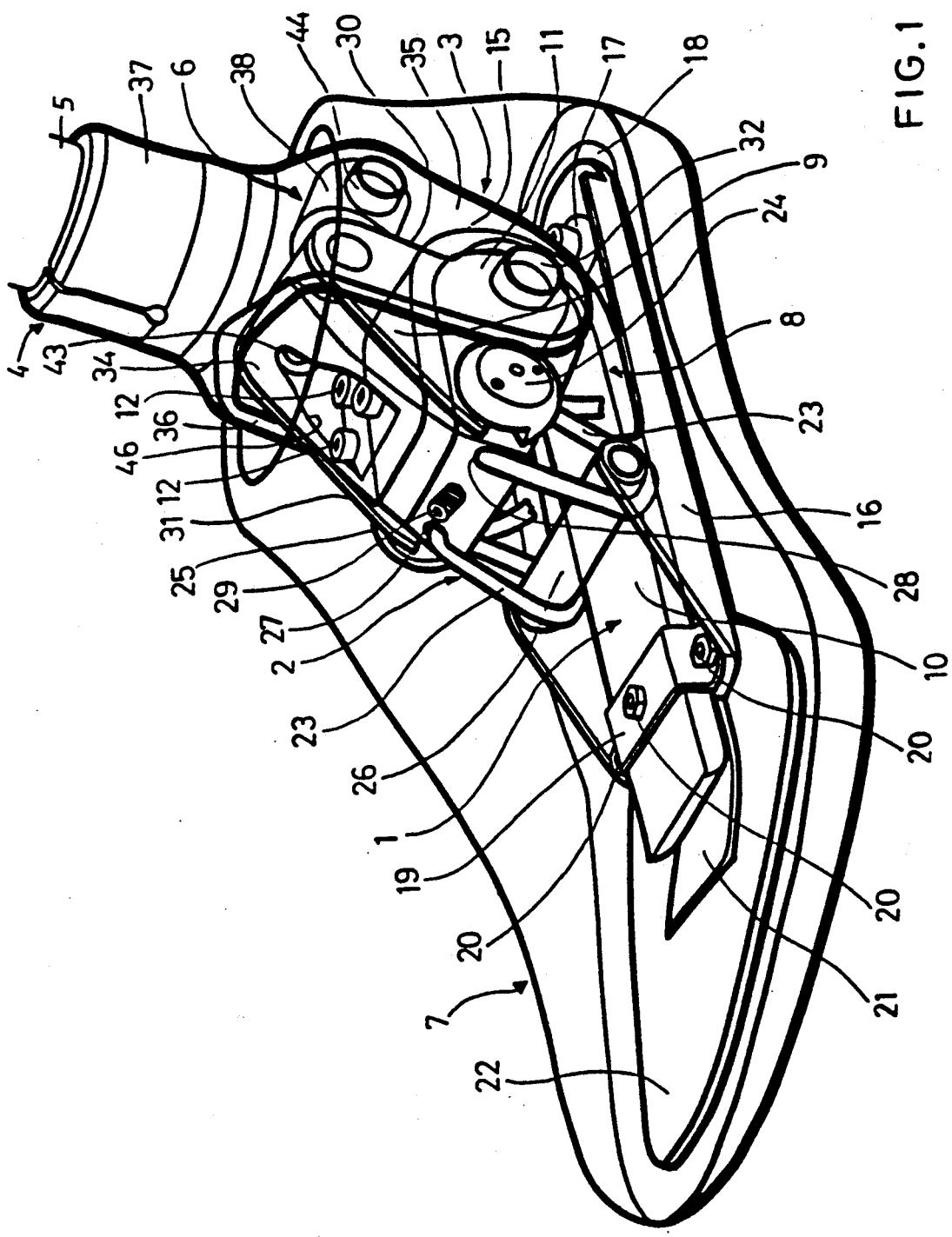
FIG. 1 is a partially transparent, perspective view of an embodiment of a prosthetic foot in accordance with the invention.
Figure 2:
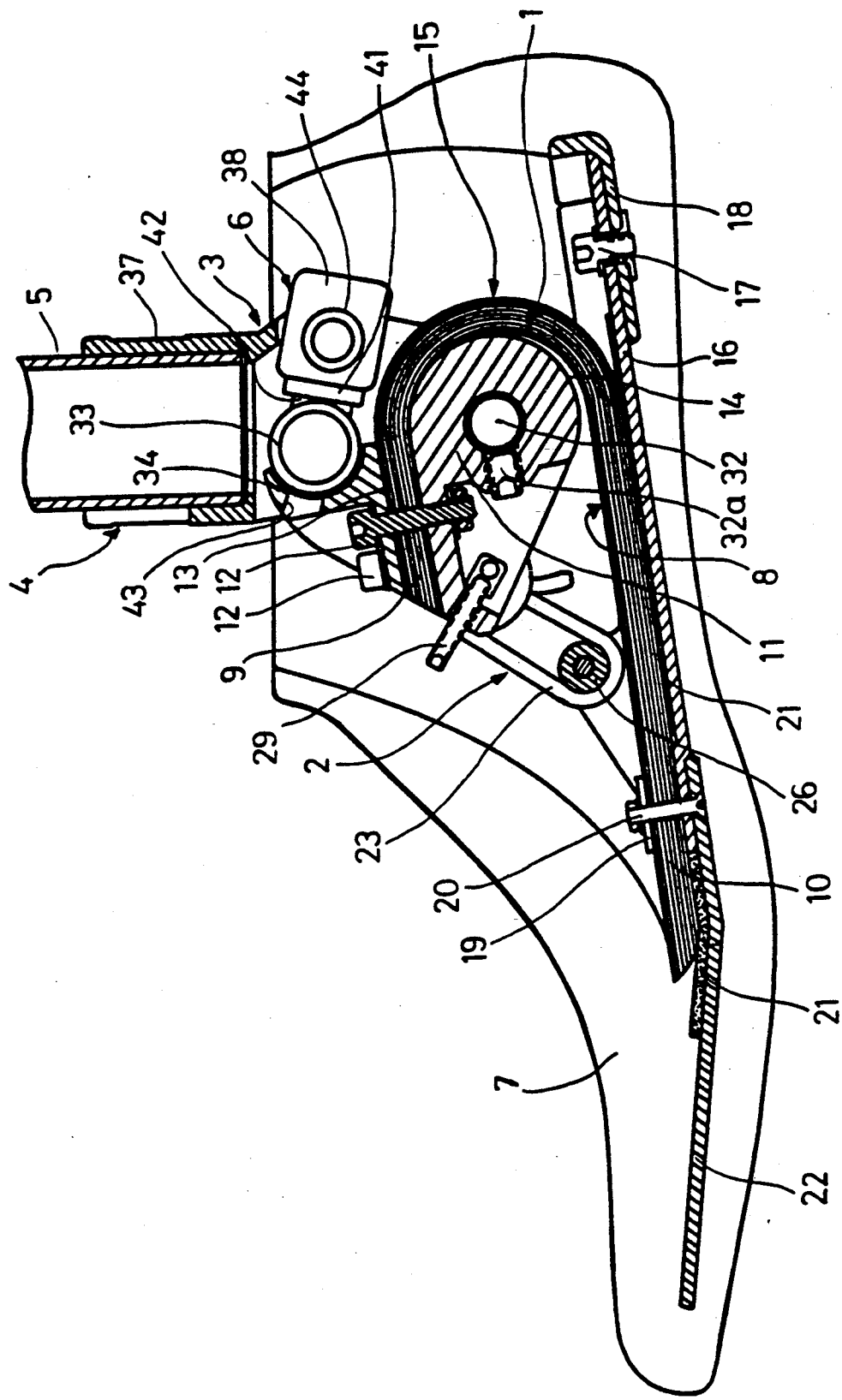
FIG. 2 is a longitudinal section through the foot of FIG. 1.

The prosthetic foot illustrated in FIGS. 1 and 2 includes as main components an elastic, energy storing spring means 1, a biasing system 2 for regulatable biasing of the spring means 1, an ankle joint member 3 pivotably connected to the spring means 1, the upper part of the member 3 being provided with a tubular adapter 4 for a lower leg tube 5, and a linkage system 6, operatively arrranged between the spring means 1 and the ankle joint member 2 for adjusting the attitude of the foot in relation to the lower leg in a rest position,—the so-called heel height. The whole arrangement is fastened in a hollow, flexible cosmesis 7, e.g. of foam plastics, which surrounds the main part of the abovementioned prosthetic foot components.

The spring means 1 comprises leaf spring element 8, preferably of composite material such as carbon/glass fibre or the like, formed into a hooklike configuration with an upper short leg portion 9 and a lower longer leg portion 10 that includes a forward portion and lower hook portion. An attachment and snubbing member 11 for the spring element 8 is fastened to the upper leg 9 of the latter, in this case with three hexagonal socket (Allen) screws 12. The attachment and snubbing member 11 has an upper straight, flat surface portion 13 functioning as fastening plane for the upper hook portion of spring element 8, and also a convex curved surface portion 14 co-acting with the inner concave surface of the spring hook 15, but with a smaller radius of curvature. The curved surface of the fastening/snubbing member 11, i.e. its snubbing path, is adapted such that the outmost point, or rather line, of the engagement of the spring element 8 against the snubbing member under load is successively moved along the snubbing path with simultaneous foreshortening of the free spring length; i.e. effective shortening of the lower spring leg 10, thereby stiffening of the spring element 8. This, which is an essential distinguishing feature of the invention, will be dealt with in more detail later on in the unloaded position, the snubber 11 is supported at least in part above the lower portion of the primary spring (FIG. 2).

The lower forward spring leg 10 rests against a bottom plate 16 with upstanding flanges, the rear part of this plate being fastened by a screw 17 to a circular plate 18 molded into the cosmesis 7. In the illustrated case, this is the sole fixation between the spring means 1 and the cosmesis 7. A shackle plate 19 fastens the forward end of the leg 10 to the bottom plate 16 with the aid of shackle screws 20. A protective diaphragm 21 is arranged between the lower leg 10 and a toe plate 22 slidably arranged in the cosmesis 7, the toe plate acting as an extension and a width increasing means of the lower spring leg 10.

The biasing system 2 for regulatable biasing of the spring means 1 includes a tensioning band 23 of suitable material, e.g. Kevlar, which from the band fastenings 24, 25 on either side of the spring means 1 extends over a roller or pulley 26 which is rotatably mounted in the bottom plate 16. The band then passes via openings 27, 28 in the front portion of the snubbing member 11 through the inner end of a set screw 29 extending into a cavity in the snubbing member 11. The band fastenings 24, 25 are each connected to plates 30, 31 pivotably mounted via bearings on an ankle joint shaft 32 extending through a bore passing through the fastening/snubbing member 11 and fixed thereto by a stop screw 32a.

At their upper parts both plates 30, 31 are connected to each other via a rotatably mounted stop roller 33 included in the above mentioned linkage system 6. The stop roller 33 is adapted for co-action with a stop 34 fastened to the upper part of the spring means 1 and provided with a concave top portion for receiving the roller 33 such as to limit the forward swinging movement of the plates 30, 31 (counter clockwise in FIG. 1).

Each band fastening 24, 25 is rotatably arranged in the respective plate 30, 31 and removably fixed, e.g. with the aid of a double toothed ring and tension nut (not shown). By loosening the clamping nuts the band fastenings can be rotated, thus altering the distance between the attachment point of the band ends and the ankle joint shaft 32, and thus the length of the "lever" acting on the tensioning band 23. As will be seen from the following, the resistance to plantar flexion can thus be increased or decreased, shorter leverage giving greater resistance and vice versa. The biasing system 2 naturally prevents delamination of the spring element 8 for plantar flexion.

Using the above mentioned set screw 29, the active length of the tensioning band 23 outside the fastening/snubbing member 11 can be foreshortened by screwing in this screw. Since the pivoting movement of the plates 30, 31 is limited by the stop 34, both spring legs 9, 10 are caused to approach each other while biasing the spring means 1. Since the latter has, as will be discussed in more detail below, a progressive characteristic, this means that increased bias gives increased spring stiffness. Conversely, the bias can be reduced by screwing out the set screw 29. By such regulation of the spring stiffness, it can be suited to the weight and degree of activity of the user. Accordingly, a light person uses a slightly biased spring while a heavier person uses a more tensioned spring.

The ankle joint member 3 has a lower bifurcated part, including legs 35, 36 which are pivotably mounted on the ankle joint shaft 32. The ankle joint member also has an upper tubular portion 37 forming the above mentioned adapter 4 for the tube 5 uniting the prosthetic foot with the prosthesis sleeve. Both leg portions 35, 36 are connected at their upper portion to a rear cylinder 38 in the linkage system 6.

Figure 3:
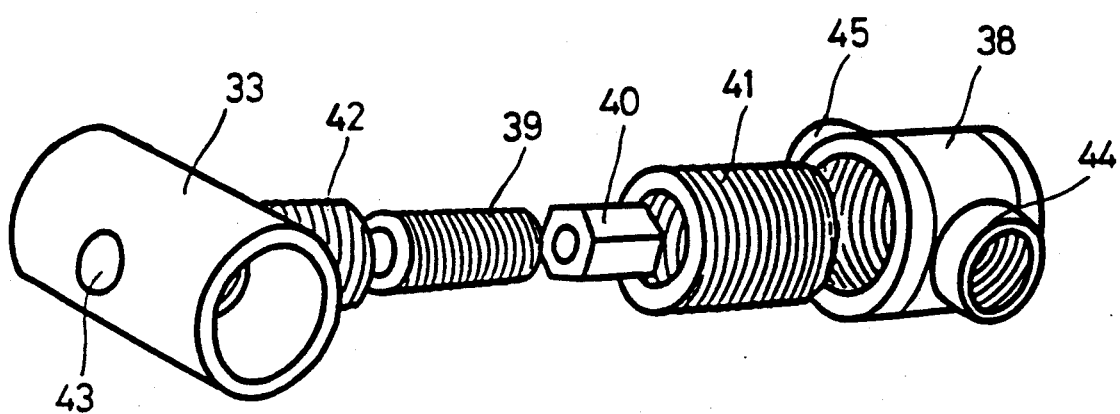
FIG. 3 is an exploded view of a linkage system included in the embodiment of FIG. 1, FIGS. 4A-C are schematic side views of the spring means in the embodiment according to FIG. 1 in different loading positions.

The detailed configuration of the linkage system 6, which functionally is a double turnbuckle, is illustrated in FIG. 3. It comprises the above mentioned stop roller 33, a stop screw 39, a hexagonal element 40, an inside and outside threaded cylinder 41 and the above mentioned rear cylinder 38.

The stop roller 33 has a central tubular projection 42, in this case externally threaded with a lefthand thread and internally threaded with a righthand thread. Directly opposite the projection 42 there is a through hole 43 made in the roller 33 for an Allen key.

The inside thread of the cylindrical projection 42 meshes with an outside righthand thread of the stop screw 39, which is screwed into the projection 42. The stop screw 39 has a central, hexagonal cavity for accommodating an Allen key inserted in the above mentioned through hole 43.

The threaded cylinder 41 has an outside righthand thread and an inside lefthand thread allowing the cylinder 41 to be screwed onto the projection 42 of the stop roller 33. The cylinder 41 is provided at its further end, i.e. to the right in the figure, with a bottom having a central hexagonal opening adapted for accommodating the hexagonal element 40, one end of which engages against the stop screw 39. The element 40 has a hexagonal cavity for a small Allen key.

The rear cylinder 38, which is rearwardly closed, has an inside righthand thread for meshing with the outside thread of the cylinder 41. In addition, the cylinder 38 has two internally threaded cylindrical cross arms 44, 45 for fixing in the legs 35, 36 of the ankle joint member 3.

The linkage system 6 described above thus connects the pivotable ankle joint member 3 with the plates 30, 31 included in the biasing system 2. Since the stop roller 33 engages against the stop 34 when the prosthetic foot is at rest, the longitudinal extension of the linkage system 6 will determine the angle of rest of the prosthetic foot in relation to the prosthesis tube 5, i.e. the so-called heel height. By extension or shortening of the linkage system 6 this angle can be changed without the positions of the band fastenings 24, 25 being affected, i.e. without affecting the biasing of the spring means 1.

In order to reset the linkage system 6, the stop screw 39 is first loosened with the aid with the aid of an Allen key inserted in its hexagonal recess via the through hole 43 in the stop roller 33. This is accessible via an opening in the cosmesis 7 and a recess 46 in the stop 34. A smaller Allen key is then inserted through the stop screw 39 and into the hexagonal element 40 for engagement therewith. The element 40 functions in turn as hexagonal key for the cylinder 41, which on being turned threads exteriorally onto the rear cylinder 38 and interiorally on the projection 42 of the stop roller 33, and is thus moved axially relative the stop cylinder 33 and the rear cylinder 38, the hexagonal element 40 moving in the hexagonal opening in the bottom of the cylinder 41. In turn this results in foreshortening or extension of the linkage system 6, according to the turning direction, and due to the functioning of the linkage system as a double turnbuckle, the final movement will be double the amount of the threads pitches described previously. Locking the system is done by screwing the stop screw 39 against the hexagonal element 40, which fixes it against the bottom of the rear cylinder 38.

Although such adjustment of the linkage system 6 is primarily intended to be carried out for compensating a changed foot angle as a result of changes in the biasing of the spring means 1 via the biasing system 2, it also enables the user to make his own adjustment for adapting the prosthetic foot to different shoes, barefoot ambulation etc.

In ambulation with the above described prosthetic foot, upon heel strike, which induces plantar flexion, i.e. downward flexion of the foot, the ankle joint member 3 will be caused to swing backwards, i.e. clockwise in FIG. 1, about the ankle joint shaft 32. The plates 30, 31 are also swung backwards on the ankle joint shaft 32 via the linkage system 6, the band fastenings 24, 25 being taken upwards so that the tension band 32 pulls the spring legs 9, 10 towards each other via the roller 26, i.e.

deflection of the spring element 8 is accomplished. The force developed on heel down is thus taken up by the spring means 1, which deflects. As previously mentioned, damping will be proportional to the spring biasing set via the biasing system 2, this being set taking into account the weight and degree of activity of the user.

When the forward part of the prosthetic foot is loaded, the ankle joint member 3 urges the stop roller 33 of the linkage system 6 against the stop 34. The lower, longer spring leg 10 is urged upwards and the tension band 23 effectively becomes slacker. On toe-off the energy stored in the spring means 1 is released. The biasing system 2 dampens the return spring movement, thus preventing resonance phenomena, which would otherwise be very uncomfortable, since the foot would vibrate at each step, particularly "at the double".

The function of the spring means 1 will now be described in more detail in the following with reference to FIGS. 4A-C.

Figure 4A:
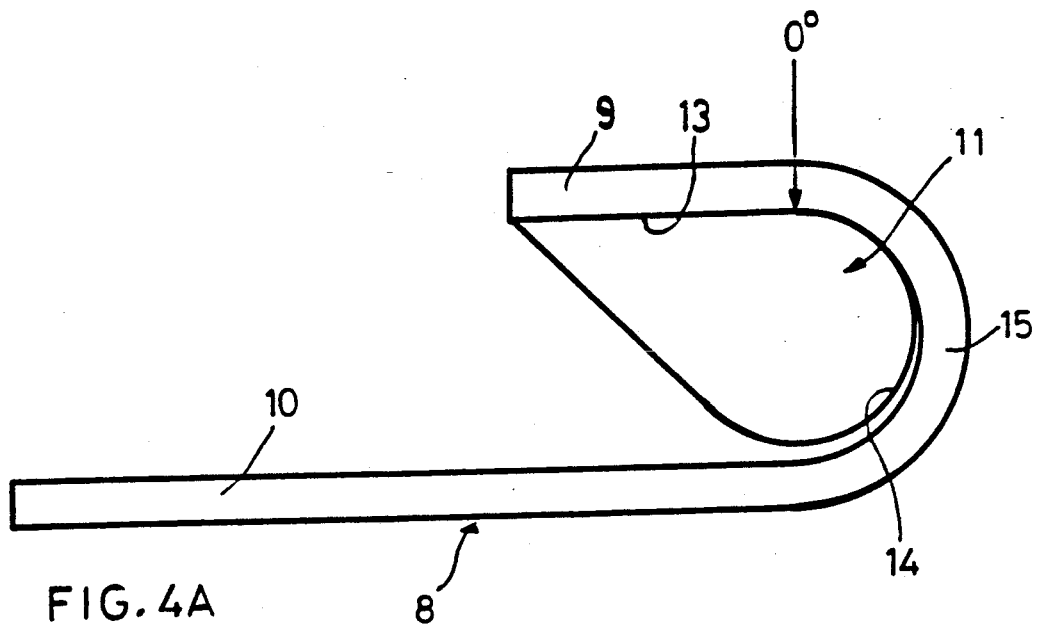

As mentioned above, the convex curved portion 14 of the attachment/snubbing element 11 and the convex curved spring portion 15 are excentrically connected such that in the illustrated case they contact each other at a point marked with 0° in FIG. 1A, the spacing between the spring and element 11 then increasing around the curved portion 14 (clockwise in FIG. 4A). When the spring means 1 is loaded so that the spring legs 9, 10 are moved together the outmost area of contact increases successively from 0° in an unloaded state to about 195° (FIG. 4C) for full load. FIG. 4B illustrates an intermediate position with about 135° of engagement. The snubbing path is here arranged to really give the spring element 8 as effective snubbing engagement as possible at each point in the entire interval from 0° to 195°.

When the spring means 1 is loaded, the spring element 8 is thus rolled little by little up on the snubbing member 11, the contact surface between them being greater and greater and the snubbing point moved to a corresponding degree along the spring element 8. The free spring length or leverage is thus shortened with accompanying stiffening of the spring. The obtained stiffening, or progressivity is proportional to the spring deflection, which is in turn proportional to the force acting on the system.

As a result of this progressivity, low activity with low loading values (such as ambulation) meets less resistance than higher activity with higher loading, e.g. running. This means that a single spring arrangement (the prosthetic foot) can be adjusted with the aid of the biasing for every individual, and can be suitably stiff for "every day activities" while at the same time it will be very effective for larger stresses such as occur in sports, due to its progressivity.

Figure 4B:
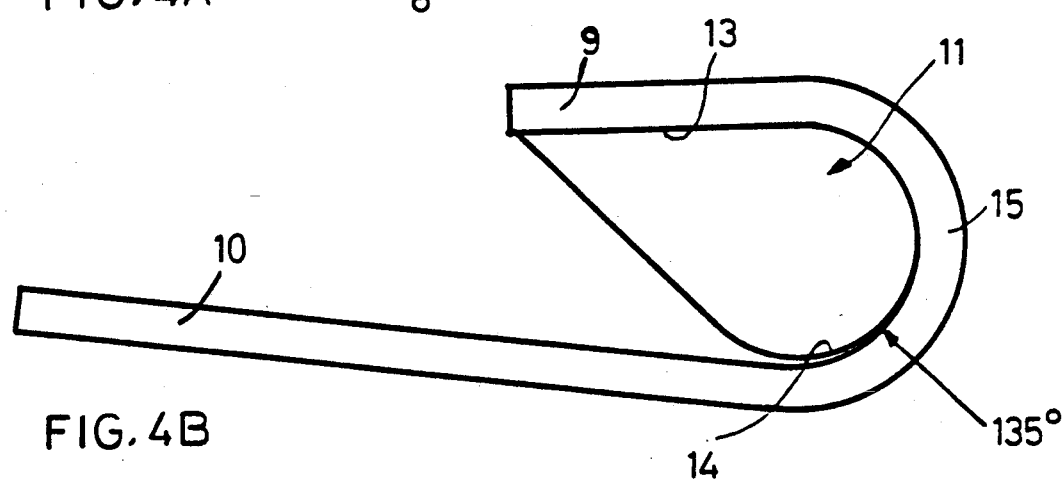
Figure 4C:
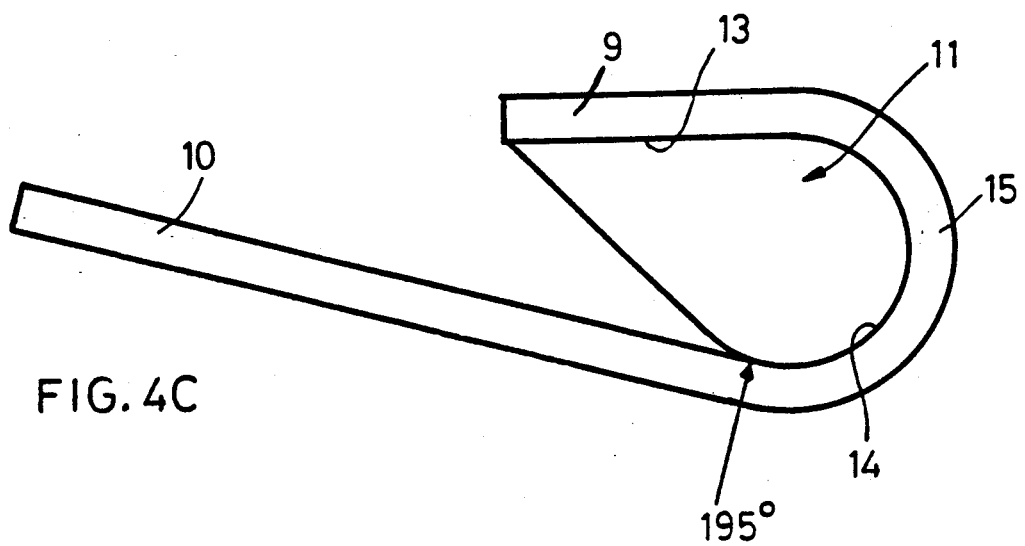
Figure 5A:
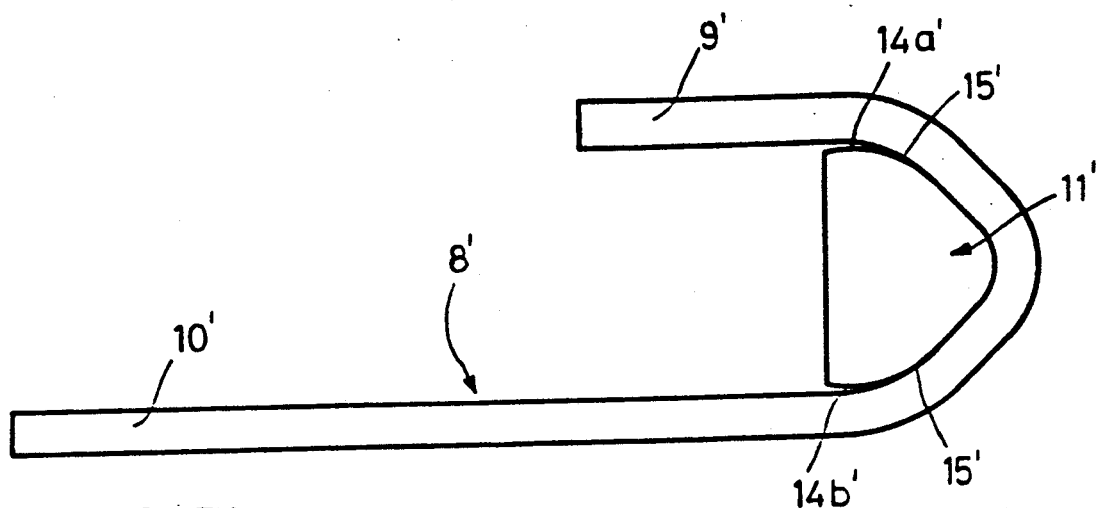
FIGS. 5A-C are schematic side views of another embodiment of the spring means in different loading positions.
Figure 5B:
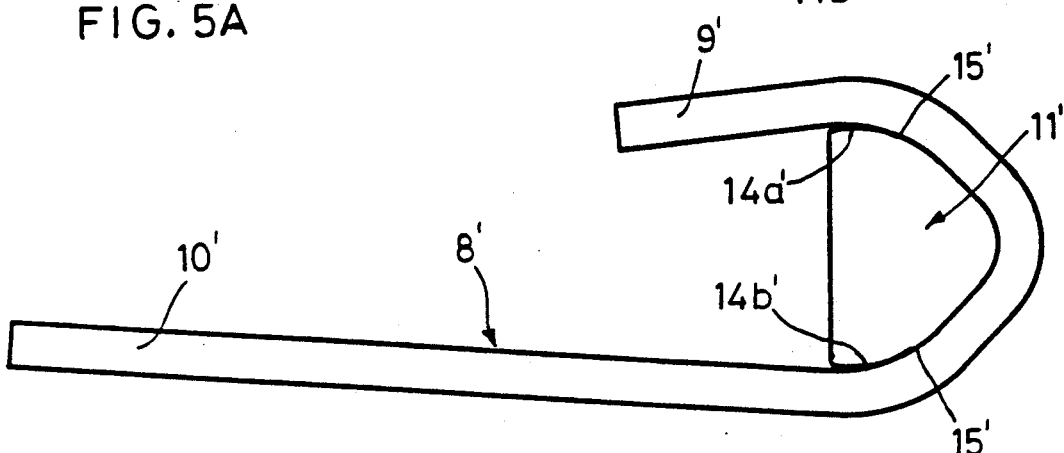
Figure 5C:
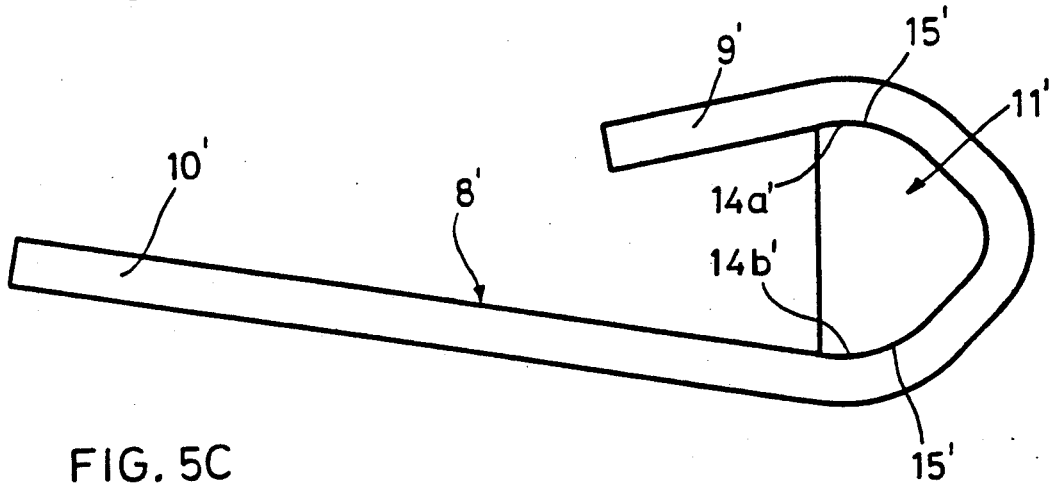

An alternative embodiment of the spring means is illustrated schematically in FIGS. 5A-C, where corresponding to the spring means of FIGS. 4A-C have the same reference numerals but with prime signs.

In this embodiment, the fastening and snubbing element 11' has two opposing snubbing paths 14a', 14b', so that the spring element 8' works simultaneously against the upper and lower sides of the snubbing element 11'.

When the spring means is loaded, an ever greater part of the inner end portion of the shorter spring leg 9' will come into engagement against the upper snubbing path 14a', simultaneously as an increasing part of the inner end portion of the spring leg 10' will come into engagement against the lower snubbing part 14b', with accompanying successive stiffening of the spring means in the same way as described above in connection with FIGS. 4A-C.

In FIG. 5A, the spring means is in unloaded state, in FIG. 5B it is somewhat loaded, and in FIG. 5C it is under full load with maximum engagement between the spring legs 9', 10' and the snubbing member 11'.

The fastening of the spring element 8' to the snubbing member 11' may here take place, for example, with the aid of an exterior casing gripping round the spring and the core. The spring member 8' may optionally be parted, i.e. it may consist of separate supper and lower spring elements 9', 10'.

With the described spring means the entire flexion takes place relatively independently of the foot cosmesis, which thus does not participate actively. Deformation occurs in the region above the ankle, where it is taken up by a resilient lower leg cosmesis. The sole is thus not deformed, and the foot cosmesis maintains its fitting to a shoe in all situations of flexure.

With the aid of the illustrated fastening of the spring means 1 in the cosmesis 7, i.e. via the bottom plate 16, which is connected to the heel and toe plates 18, 22 molded into the cosmesis 7, there is formed a relatively stiff element along the entire length of the sole. This results in effective transmission of loading forces to the spring means 1 with minimum dampening in the fastening components. There is thus prevented the relatively large deformation with accompanying wear, which is usually present in energy absorbing/releasing prosthetic feet.

FIG. 6 shows a view corresponding to FIG. 2 illustrating an alternative embodiment of the foot cosmesis, with corresponding parts being identified by the same reference numerals as shown in FIG. 2 with the addition of 100. Thus, the spring means 101 comprises leaf spring element 108 formed into a hook like configuration with an upper forwardly extending short leg 109 and a lower leg 110. Snubbing member 111 is attached to the upper portion 109 of the spring element 108. In this example, the upper leg 109 is inserted into the snubber 111 and retained therein. The snubber 111 is provided with a convex curved portion 114 coacting with an inner concave surface of the hook portion of the spring 115. The ankle joint and leg adapter are pivotally connected to the snubber 111 at ankle joint shaft 132 and the tension band 102, 123 is wrapped around the lower pulley 126 to provide the same arrangement as illustrated in FIG. 2. Thus, forward pivotal motion of the ankle joint relative to the foot cosmesis causes external convex surface 114 of snubber 111 to progressively wrap the lower section of the hook portion 115 of spring 111 about the convex surface 114 to shorten the effective length of the spring 108. Rearward pivotal movement of the ankle joint about axis 132 is transmitted to the upper section 109 of spring 108 via tension band 102, 123 in the same manner as described previously.

In summary, the prosthetic foot illustrated in the drawing figures provides very good comfort for the user in all situtions. The progressive springing makes the prosthetic foot usable for both normal activities and those which produce greater loading. In addition, a single spring member absorbs deflection forces in both dorsal and plantar flexion. The regulatable biasing arrangement allows adjustment of the prosthetic foot to patients having different weights, and optionally also to different degrees of activity. A corresponding adjustment of the resistance to plantar flexion is achieved by adjusting the position of the tension band fastenings relative to the ankle joint. Finally, the heel height can be easily adjusted by the user himself, without affecting the damping properties of the foot.

The invention is of course not restricted to the embodiments described above and particularly illustrated, but many variations and modifications are obvious to one skilled in the art within the scope of the general inventive concept, as it is disclosed in the following claims.

I claim:

1. In a foot prosthesis including a hollow cosmesis, a spring means fastened in the cosmesis and extending in a longitudinal direction of the cosmesis for storing energy on heel strike and releasing energy on toe-off, an ankle joint connected to the foot cosmesis and a leg adapter for connecting the foot prosthesis to a leg connected to the ankle joint, the improvement comprising:

said spring means comprising a forward lower portion extending generally parallel with the lower portion of the foot cosmesis and anchored in the forward lower portion of the foot cosmesis, a rearwardly located hook portion including a lower section connected to the lower portion and an upwardly and forwardly extending bent hook section including an upper terminal section connected to and extending forwardly from the forwardly bent section so as to lie above said lower section;

a snubbing means for transmitting load from the leg adapter to the spring means via the ankle joint, said snubbing means secured to the upper terminal section of the spring means;

said hook portion having a concave curved inner surface having a first geometric contour and said snubbing means having a convex curved outer surface having a second geometric contour smaller than the curvature of said hook portion, said snubbing means disposed within said hook portion with said snubbing means convex outer surface extending along said hook portion concave inner surface over a limited portion of said snubber outer surface so as to leave a free length of said hook portion not engaging the snubbing means;

said snubbing means connected to the upper terminal section of the spring such that a lower portion of said convex curved outer surface is normally spaced above the forward lower portion of the spring means when the foot prosthesis is unloaded vertically, and such that forward pivotal motion of the leg adapter relative to the foot cosmesis causes the inner surface of the hook portion to progressively wrap around the outer surface of the snubber means to effectively foreshorten the effective length of the primary spring means and to thereby vary the spring rate of the spring means;

whereby increasing forward pivotal motion of the leg prosthesis produces a progressively increasing spring rate producing a progressively higher force resisting such forward pivotal motion.

2. The improvement as claimed in claim 1 including means for transmitting ankle joint rearward flexion motion to said upper terminal section of the hook portion of the spring means via said snubber to cause progressive bending of the spring hook portion about said snubber convex curved outer surface upon rearward flexion ankle joint motion.

3. The improvement as claimed in claim 2, including means for varying the amount of ankle joint rearward flexion motion transmitted to the motion transmitting means upon rearward flexion movement of the ankle joint.

4. The improvement as claimed in claim 2, wherein said ankle joint includes a transverse flexion pivot axis, and said motion transmitting means comprises a tension element extending continuously from a forward portion of said snubber above and forwardly of said flexion pivot axis to a pulley located at the lower forward portion of the foot cosmesis at a location in front of said snubber and to an attachment zone on the ankle joint that is movable with the ankle joint and located at a radius relative to said pivot axis, whereby upon rearward pivotal movement of said ankle joint relative to the foot cosmesis, said band transmits motion of the ankle joint to the upper terminal section of the hook portion via the snubber to draw the upper terminal section towards the pulley.

5. The improvement as claimed in claim 4 including means for applying a pretension force to said upper terminal section of the hook portion via said tension element whereby the spring is pretensioned when the foot cosmesis is unloaded.

6. The improvement as claimed in claim 2, wherein said ankle joint includes a transverse flexion pivot axis, and said motion transmitting means comprises a tension element extending continuously from a forward portion of said snubber above and forwardly of said flexion pivot axis to a pulley located at the lower forward portion of the foot cosmesis at a location in front of said snubber and to an attachment zone on the ankle joint that is movable with the ankle joint and located at a radius relative to the pivot axis, whereby upon rearward pivotal movement of said ankle joint relative to the foot cosmesis, said band transmits motion of the leg adapter to the upper terminal section of the hook portion via the snubber to draw the upper terminal section towards the pulley, including means for varying the amount of ankle joint rearward flexion motion transmitted to the tension element upon rearward flexion movement of the ankle joint.

7. The improvement as claimed in claim 6, wherein said means for varying transmitted ankle joint movement includes means for adjusting the radius distance between said transverse flexion pivot axis and the attachment zone for the tension element on the ankle joint.

8. The improvement as claimed in claim 1, including means for adjusting the relaxed position of the leg adapter relative to the snubber, said adjusting means being operable without affecting the relative positions of the snubber and the spring means.

9. The improvement as claimed in claim 8, wherein said adjusting means includes a variable length turnbuckle accessible from outside the foot prosthesis.

10. The improvement as claimed in claim 1 wherein said snubbing means comprises a resilient material having greater stiffness than said spring.

* * * * *